United States Patent [19]

Brackenridge et al.

[11] Patent Number: 5,039,729

[45] Date of Patent: Aug. 13, 1991

[54] NOVEL MIXTURES OF BROMINATED DIPHENYL ETHANES

[75] Inventors: David R. Brackenridge; Saadat Hussain, both of Baton Rouge, La.

[73] Assignee: Ethyl Corporation, Richmond, Va.

[21] Appl. No.: 487,879

[22] Filed: Mar. 5, 1990

[51] Int. Cl.$^5$ .......................... C08K 5/03; C09K 21/08
[52] U.S. Cl. .................................... 524/412; 252/609; 524/466; 570/184
[58] Field of Search ............... 524/466, 469, 471, 412; 570/184; 252/609

[56] References Cited

U.S. PATENT DOCUMENTS

| | | | |
|---|---|---|---|
| 2,033,612 | 3/1936 | Clark et al. | 570/184 |
| 2,244,284 | 6/1941 | Britton et al. | 570/184 |
| 3,141,860 | 7/1964 | Sauer et al. | 524/412 |
| 4,666,947 | 5/1987 | Brichta et al. | 524/471 |

OTHER PUBLICATIONS

Joseph Green et al., "Flame Retarding Thermoplastic Styrenic Resins", *Fire Retardants; Proceedings of 1974 International Symposium on Flammability and Fire Retardants*, May 1-2, 1974, Ontario, Canada Technomic Pub. Co. (1975).

*Primary Examiner*—Veronica P. Hoke
*Attorney, Agent, or Firm*—Edgar E. Spielman, Jr.

[57] ABSTRACT

This invention relates to novel mixtures of brominated diphenyl ethanes, such mixtures containing a predominant amount of hexabromodiphenyl ethane and having an average bromine number, based upon GC area percent, of from about 6.7 to about 7.3. ABS based formulations containing such mixtures and articles made from such formulations are also a part of this invention.

22 Claims, No Drawings

NOVEL MIXTURES OF BROMINATED DIPHENYL ETHANES

BACKGROUND OF THE INVENTION

This invention relates to novel mixtures of brominated diphenyl ethanes, which mixtures impart good flame retardancy to acrylonitrile-butadine-styrene (ABS) based formulations.

ABS based formulations are used widely in the manufacture of pipes, automobile parts, and housings for business machine and telephones. In many of these uses, it is required that the articles have a flame retardant quality. Such quality can be obtained by incorporating a flame retardant, e.g. a mixture of brominated diphenyl oxides, in the formulation. Especially useful brominated diphenyl oxide mixtures are those which have an average of from about 7.0 to about 7.7 bromine atoms per molecule of diphenyl oxide and which contain 0-2 weight percent pentabromodiphenyl oxide, 5-15 weight percent hexabromodiphenyl oxide, 40-55 weight percent heptabromodiphenyl oxide, 30-40 weight percent octabromodiphenyl oxide, 5-15 weight percent nonabromodiphenyl oxide, and 0-2 weight percent decabromodiphenyl oxide. These mixtures are commercially available or can be easily prepared by the reaction of bromine with diphenyl oxide in the presence of a bromination catalyst, such as, $ZrCl_4$. See U.S. Pat. No. 4,740,629.

While these mixtures give ABS based formulations a flame retardant quality, they are not a panacea as their presence can reduce the impact strength of articles made from such formulations.

THE INVENTION

This invention provides for novel mixtures of brominated diphenyl ethanes, such mixtures having a bromine average number, based upon gas chromatographic (GC) area percent, of from about 6.8 to about 7.2. These mixtures contain hexabromodiphenyl ethane, heptabromodiphenyl ethane and octabromodiphenyl ethane with the amount of hexabromodiphenyl ethane being greater than or equal to the sum of the amounts of the hepta- and octabromodiphenyl ethane in the mixture. Other bromo homologs may be in the mixture, such as, pentabromodiphenyl ethane, nonabromodiphenyl ethane and decabromodiphenyl ethane.

This invention also provides for ABS based formulations containing: ABS resin; a mixture of brominated diphenyl ethanes as described above; and, optionally, a flame retardant synergist. These formulations can be used to produce articles having good flame retardancy and a good percentage of the impact strength which is characteristic of the ABS resin used in the formulation.

The ABS resin used in the formulations of this invention can be any of those which are denominated by the art as high impact, medium impact, low impact or heat resistant. The ABS resin can be comprised of any suitable proportion of acrylonitrile, rubber or styrene. The resin can also be any of those produced by the well known emulsion, suspension or batch processes. Even further, the resin may have units other than acrylonitrile, butadiene and styrene. For example, methylmethacrylate can be copolymerized therewith. Also, other polymers may be used to modify the ABS resin, such other polymers including modified styrene resins, such as rubber modified polystyrenes, and the styrene containing copolymers, such as the styrene-acrylonitrile copolymers, styrene-butadiene copolymers, styrene-acrylonitrile-α-alkyl styrene copolymers, poly-α-methyl styrene, copolymers of ethylvinylbenzene and divinylbenzene, and the like. The preferred resin is unmodified acrylonitrile-butadiene-styrene. For a further discussion of suitable ABS resins, see Kirk-Othmer Encyclopedia of Chemical Technology, 3rd edition, John Wiley & Sons, Vol. 1, pages 442-456, and Encyclopedia of Polymer Science and Technology, John Wiley & Sons, Vol. 1, pages 436-444, all of which are incorporated herein by reference as if fully set forth.

From a processing standpoint, the more preferred ABS resins are those which are classified as medium and low impact. The ABS resin used in the formulations of this invention is present in a predominant amount. Generally, the ABS resin will account for from about 70 weight percent to about 90 weight percent of the formulation. Preferred amounts are within the range of from about 75 weight percent to about 90 weight percent.

The average bromine number, used in specifying the mixtures of this invention, is defined as the average number of bromine atoms per molecule of brominated diphenyl ethane in the mixture. The average bromine number can be calculated by multiplying the GC area percent or the weight percent of each bromo homolog in the mixture by the number of bromine atoms in that homolog, adding the resulting product and dividing the sum by 100. There will be a slight variation between the average bromine number obtained when using GC area percent and when using weight percent. This variation is the result of the GC area percent not always accurately reflect the quantitative relationship between the different bromo homologs in the mixture, which inaccuracy is due to the GC response being different for various of the bromo homologs. The variation between GC area percent and weight percent can be resolved by multiplying the GC response factor for each bromo homolog times the GC area percent for that homolog. The product will give the weight percent. For the mixtures of this invention, preferred average bromine numbers, based upon GC area percent, are within the range of from about 6.7 to about 7.3, with an average bromine number of from about 6.9 to about 7.1 being most preferred. Most highly preferred are average bromine numbers of from about 7.0 to about 7.07.

For the purposes of obtaining the GC area percents and the identities of the bromo homologs which form the mixtures of this invention, a combination of gas chromatography and mass spectrometry can be used. The mass spectrometer is used to identify each bromo homolog and correlate its identity with the particular peak(s) and retention time(s) shown by the gas chromatogram.

It is recognized that the GC area percent values for each bromo homolog may vary slightly dependent upon the particular gas chromatograph used and upon the analytical conditions used in operating the gas chromatograph. To provide a standard for obtaining the GC area percent values used herein, the following is given:

Gas Chromatography
Instrument—Hewlitt Packard HP5780-A
Column—10 meter, DB-1 methyl silicone megabore, made by J&W Scientific of California
Program—200°-300° C., at 5./min +20 min. hold at 300° C.
Injector—285° C., split injector, Hewlitt Packard
Detector—325° .C FID (flame ionization detector)

Sample Size—1 μL (1% soln) +1 μL methylene bromide plug

The response factors used in obtaining the weight percent values recited herein are approximates which are based upon empirical observation and experience in quantifying the bromo homologs in various flame retardants.

| Bromo homolog | Response Factor |
|---|---|
| DPE-BR$_4$ | 0.85 |
| DPE-BR$_5$ | 0.85 |
| DPE-BR$_6$ | 0.9 |
| DPE-BR$_7$ | 0.9 |
| DPE-BR$_8$ | 1.0 |
| DPE-BR$_9$ | 1.1 |
| DPE-BR$_{10}$ | 1.1 |

More exact response factors can be obtained by conventionally comparing the GC area percents for a standard amount of each individual brominated homolog against one another.

On the bases of GC area percent, a typical bromo homolog distribution for the mixtures of this invention is, 0-2 GC area percent pentabromodiphenyl ethane, 40-55 GC area percent hexabromodiphenyl ethane, 12-25 GC area percent heptabromodiphenyl ethane, 15-25 GC area percent octabromodiphenyl ethane, 10-15 GC area percent nonabromodiphenyl ethane, and 0-5 GC area percent decabromodiphenyl ethane. The mixture can also contain some impurities, usually less than 1.5 GC area percent. On the basis of weight percent, this typical mixture will contain 0-2 weight percent pentabromodiphenyl ethane, 34-47 weight percent hexabromodiphenyl ethane, 11-23 weight percent heptabromodiphenyl ethane, 15-25 weight percent octabromodiphenyl ethane, 11-17 weight percent nonabromodiphenyl ethane, and 0-6 weight percent decabromodiphenyl ethane, all derived from the product of the above given response factors and the above recited GC area percent values for each bromo homolog.

As can be seen, the bromo homolog distribution for mixtures of this invention considerably favors hexabromodiphenyl ethane. This distribution is not considered normal for a mixture having an average bromine number from about 6.8 to about 7.2 as it would be expected that, instead, the heptabromo homolog would be favored and that the mixture would have a more Gaussian distribution.

A process for producing the brominated diphenyl ethane mixtures of this invention is illustrated in the Examples. Generally, the process recited in the Examples comprises: charging a reactor with diphenyl ethane, a solvent and a catalytic amount of AlCl$_3$; adding bromine to the so-charged reactor while maintaining the reactor contents at a temperature within the range of from about 5° C. to about 20° C.; bringing the reactor contents to a temperature within the range of from about 0° C. to about 60° C. and maintaining such a temperature until the bromination is completed, generally over a time period of from about 1.0 to about 2.5 hours. Two signs can be used to determine that the bromine reaction has been completed. One sign is that the reactor content will lose its reddish color upon completion of the bromination. The other sign that can be used in determining bromination completion, is the cessation of HBr from the reactor contents. The amount of AlCl$_3$ used is preferably from about 0.05 moles to about 0.10 moles of AlCl$_3$ per mole of diphenyl ethane.

The bromine addition is generally completed within about 0.5 hours to about 2.5 hours. The solvent is preferably methylene bromide, i.e. CH$_2$Br$_2$, but other solvents may be used provided that such solvents do not have an adverse affect on process yield or bromo homolog distribution. The molar ratio of diphenyl ethane to bromine (Br$_2$) added is essentially that amount needed to obtain an average bromine number from 6.7 to 7.3, i.e., a molar ratio of 1:6.7 to 1:7.3 plus that amount of bromine, if needed, to make up for any bromine lost from the reactor or used in side reactions. After all of the added bromine has been reacted, the brominated diphenyl ethane mixture can be recovered by first contacting the reactor contents with a precipitating agent, i.e. an alkanol such as MeOH, and then filtering the reactor contents to recover the solid brominated diphenyl ethane mixture therefrom. The volume ratio of alkanol to reaction mass is preferably from about 1:1 to about 3:1. The alkanol can be added to the reaction mass or vice versa. For large scale runs, it is believed that it will be preferred to add the reaction mass to the alkanol. Another recovery method entails steam stripping the solvent from the reaction mass.

The foregoing process is unusual in that it uses AlCl$_3$ as the bromination catalyst. The art recognizes AlCl$_3$ to be a very strong bromination catalyst and it is commonly used to produce perbrominated diphenyl compounds. It would thus be expected that, if AlCl$_3$ is used in producing brominated diphenyl compounds, the bromo homolog distribution would favor the higher brominated homologs. Instead, the above process unexpectedly produces a mixture in which the hexabromo homolog is favored over the more brominated hepta- and octabromo homologs.

The diphenyl ethane reactant used in the process can be produced by the reaction of benzene and alkylene dihalide in the presence of AlCl$_3$. See CA 97 38651d (Japanese Kokai 82/45114) and CA 46 7084g.

The brominated diphenyl ethane mixture is used in the ABS based formulations of this invention in a flame retardant amount. This amount is generally from about 12 weight percent to about 25 weight percent, based upon the total weight of the formulation. It is preferred that the formulations also contain any of the well known flame retardant synergists which are commonly used with halogen containing flame retardants. Such synergists enhance the flame retardant qualities of the brominated diphenyl ethanes in the mixture and thus enable the use of lesser amounts of the mixture to obtain the desired flame retardant effect. Examples of such synergists are Sb$_2$O$_3$, Sb$_2$O$_4$, and Sb$_2$O$_5$, zinc oxide, zinc borate, various inorganic bismuth compounds and organic compounds, such as, tris-2-chloroethylphosphate, tris-2,3-dibromopropyl-phosphate, etc. The most preferred synergist is Sb$_2$O$_3$.

The flame retardant synergist will generally be used in an amount, based upon the total weight of the ABS based formulation, which is within the range of from about 2 weight percent to about 6 weight percent. When a flame retardant synergist is used, the amount of brominated diphenyl ethane mixture used is preferably within the range of from about 10 weight percent to about 20 weight percent.

The constituents of the ABS based formulation of this invention can be blended one with the other in any order and by way of any conventional technique. A Branbury mixer or twin screw extruder can be used.

The ABS based formulation can also contain conventional additives, for examples, plasticizers, pigments, antioxidants, fillers, e.g. talc, glass, etc., UV stabilizers, processing aids and the like.

Conventional article forming techniques can be used to form articles from the ABS based formulations of this invention. For example injection molding, compression molding, and extrusion molding are all suitable.

The following Examples illustrate some of the features of the inventions hereinabove disclosed and are not to be taken as limiting such inventions.

EXAMPLES

The following equipment was used in Examples I and II. A 500 mL, 5-necked reaction flask was fitted with a Friedrich's condenser modified for use as a dry-ice/IPA cold-finger condenser. The reactor overhead led from the condenser exit to an oil bubbler charged with inert fluorocarbon oil, a safety trap and a tared caustic trap. The dip-leg to the caustic trap was positioned just below the liquid surface; the trap itself was placed on a balance to measure HBr evolution quantitatively with reaction time. Alternatively, the trap could be stirred magnetically if HBr weight was not a concern. A nitrogen line was tied into the overhead, downstream from the condenser. A 3-way Teflon stopcock allowed a $N_2$ purge to maintain positive pressure when HBr flow became weak, thus preventing caustic suck-back. To clear most of the residual HBr from the system, the nitrogen purge could be transferred to the 3-way stopcock on the side-arm of the empty bromine addition funnel. With the stopcock open, the addition funnel, reactor and condenser vapor spaces could be flushed at a controlled rate. The addition funnel itself was fitted with a 2 mm, metered Teflon stopcock. A thermocouple-thermowell was placed in the fourth reactor neck; the fifth neck was used for catalyst addition.

EXAMPLE I

The reactor was charged with 18.2 g (0.10M) diphenyl ethane, hereinafter DPE, and methylene bromide (50 mL), the solution was chilled to 6.C and $AlCl_3$ (0.87 g) was added. Bromine (112.0 g, 0.70 M) was added over 1.0 hours at 6°-8 C. Solids deposition was observed at ~61% bromine addition. The yellow mixture was heated over 0.3 hours to 18° C., yielding a tan slurry. Heating continued over 1.2 hours to 54° C. maximum.

Methanol (100 mL) was added dropwise at 65° C. (the first few drops turned the slurry white) over 0.4 hours. The thick, white slurry was cooled, filtered, washed with methanol and air-dried to give a white powder (69.3 g, 94.3% yield). The bromo homolog distribution and average bromine number are given in Table I. The filtrate/wash residue was obtained as a gummy solid. This was leached twice with methanol and air-dried to give a tan powder (5.0 g).

EXAMPLE II (Comparative Example)

The reactor Was charged with DpE (18.2 g, 0.10M) and methylene bromine (50 mL). The reactor was chilled to 8° C. and $FeBr_3$ (1.04 g) was added. Bromine (112.0 g, 0.70M) was added over 0.8 hours at 8°-15° C.; solids formation occurred with ~81% bromine charged. The slurry was then heated to 89° C. over 1.8 hours, when additional bromine (3.1 g) was added to compensate for a small overhead loss past the condenser cold-finger. The mixture was heated an additional 1.0 hour at 87°-95° C., giving 97.1% HBr theory in the caustic trap.

The mixture was cooled to 70° C. and methanol (100 mL) was added over 0.3 hours at slow reflux. Solvent color persisted, but small particles of white solids were observed on the reactor walls. After cooling, the reaction mass was filtered and the filter cake slurry-washed several times until the filtrate was colorless. Drying gave a white powder (72.2 g, 98.2% yield). The bromine content and the bromo homolog distribution is given in Table I.

EXAMPLE III

A 3-liter resin kettle was charged with DPE (145.8 g, 0.80M) and methylene bromide (400 mL). The kettle was sealed and the contents stirred while cooling the solution in an icebath. At ~6° C., $AlCl_3$ (7.62 g) was charged to the reactor, while bromine (894.9 g, 5.60M) was transferred to the 500 mL addition funnel. The bromine was added over 1.3 hours at 6°-9C.; solids formed with only ~38% bromine charged. An additional increment of bromine (3.1 g, 0.019M) was added to compensate for overhead losses past the cold-finger. The thick slurry was heated, over 2.0 hours, to 50° C. and gave a dark-tan slurry. Methanol (800 mL) was added, over 0.5 hours, at slow reflux to yield a cream-colored mixture containing lumpy solids instead of fine crystals. The cooled mixture was filtered, washed and the solids air-dried. After grinding with a mortar and pestle, the product was again air-dried to give an off-white powder (548.0 g, 93.2% yield)

EXAMPLE IV

The resin kettle used in Example III was charged with DPE (150.8 g, 0.837M) and methylene bromide (415 mL) and the solution was stirred. The curved adapters leading from the cold-finger and the addition funnel were modified with the addition of 3-inch extensions to help contain bromine vapor in the reactor. After cooling to 5° C., $AlCl_3$ (8.0 g) was charged and bromine (939.0 g, 5.876M, 7.10 equiv.) was transferred to the addition funnel. The bromine was added over 2.1 hours at 7°-9° C.; solids formation began with ~41% charged. The yellow-tan slurry was heated, over 2.2 hours, to 57° C.; methanol (830 mL) was added, over 1.3 hours, at 57°-69° C. Large, tan particles separated with ~50% methanol charged.

The product was worked up as before, to give (after grinding) a dark-tan powder (578.3 g, 94.2% yield). This material was charged to a 3-liter reactor with C.P. acetone (1-liter); the slurry was stirred at reflux for 0.5 hours. After cooling, the solids were filtered, washed with cold acetone (200 mL) and air-dried to give an off white powder (539.4 g, 87.9% yield) which was comparable to the product of Example III. The dark-yellow acetone filtrate was concentrated to 200 mL and cooled. The resulting precipitate was filtered and dried to give a white powder (21.0 g, 3.4% yield) which was blended with the main product. Total solvent removal gave a yellow, gummy material (13.4 g) which was not mixed with the product.

EXAMPLE V

The products of both Examples III and IV were blended manually. After blending, the particle size was unacceptable (58.5 $\mu$ average). The blend was then airmilled to give a much smaller particle (5.4 μaverage) which was suitable for mixing with ABS resin. The average bromine number and the bromo homolog distribution for this product blend is given in Table I.

TABLE I

| | Product from Example No. | | |
|---|---|---|---|
| Constituent | I GC area % | II GC area % | V GC area % |
| DPE-BR$_4$ | — | — | 0.09 |
| DPE-BR$_5$ | 1.10 | 0.17 | 2.76 |
| DPE-BR$_6$ | 48.29 | 36.70 | 41.68 |
| DPE-BR$_7$ | 15.52 | 27.95 | 17.83 |
| DPE-BR$_8$ | 17.15 | 22.53 | 20.55 |
| DPE-BR$_9$ | 13.92 | 10.42 | 12.70 |
| DPE-BR$_{10}$ | 2.78 | 2.24 | 2.52 |
| Light ends | 1.24 | — | 1.97 |
| Melting Point Range | 163–210° C. | 150–210° C. | 150–205° C. |
| Average Br Number* | 7.03 | 7.13 | 7.06 |

*Average Br number for Examples I and V obtained by normalizing GC Area % to not include Light Ends As can be seen from the Table, the mixtures of this invention principally contain the hexa-, hepta- and octabromo homologs, with the predominate amount belonging to the hexabromo homolog. Despite this distribution, the average bromine number, based upon GC area percent, is 7.02 and 7.06 for Examples I and II, respectively.

EXAMPLE IX

Three ABS-based formulations were prepared using a Brabender mixer. Two fo the formulations contained 4 weight percent Sb$_2$O$_3$, 77.3 weight percent Cycolac T-1000, an ABS resin sold by Borg-Warner Corporation (now General Electric Company), and 18.7 weight percent of the brominated diphenyl ethane mixture from Example I or Example II. The third formulation contained 10 weight percent Cycolac T-1000. Each formulation was compression molded at a temperature of 177° C. and at a molding pressure of 1400–1800 grammeter torque to form test specimens which are identified in Talbe II in accordance with the formulation used to produce each speciment.

TABLE II

| Test Specimen | Formulation Composition | UL-94 Rating | ASTM D 256 Izod Impact ⅛" notch Ft.lb/in. notch |
|---|---|---|---|
| 1 | Cycolac T-1000 Example I mixture Sb$_2$O$_3$ | V-O | 1.5 |
| 2 | Cycolac T-1000 Example II mixture Sb$_2$O$_3$ | V-O | 0.90 |
| 3 | Cycolac T-1000 | burn | 4.6 |

As can be seen from Table II, a brominated diphenyl ethane mixture of this invention (Specimen No. 1) gave a UL-94 V-O rating with less of an adverse affect on the specimen's Izod Impact strength than was realized when using a diphenyl ethane mixture not of this invention.

What is claimed:

1. A mixture of brominated diphenyl ethanes, said mixture having an average bromine number, based upon gas chromotographic area percent, which is in the range of from about 6.8 to about 7.2 and containing hexabromodiphenyl ethane, heptabromodiphenyl ethane and octabromodiphenyl ethane, in which the hexabromodiphenyl ethane is present in an amount which is greater than or equal to the sum of the amount of heptabromodiphenyl ethane and the amount of octabromodiphenyl ethane in the mixture.

2. The mixture of claim 1 wherein said mixture additionally contains nonabromodiphenyl ethane and, optionally, one or more of tetrabromodiphenyl ethane, pentabromodiphenyl ethane and decabromodiphenyl ethane.

3. The mixture of claim 1 wherein said mixture contains from about zero to about 2 weight percent pentabromodiphenyl ethane, from about 34 to about 47 weight percent hexabromodiphenyl ethane, from about 11 to about 23 weight percent heptabromodiphenyl ethane, from about 15 to about 25 weight percent octabromodiphenyl ethane, from about 11 to about 17 weight percent nonabromodiphenyl ethane and from about zero to about 6 weight percent decabromodiphenyl ethane.

4. The mixture of claim 1 wherein said mixture, when subjected to gas chromatographic analyses, yields a gas chromatogram with from about zero to about 2 area percent for pentabromodiphenyl ethane, from about 40 to about 55 area percent for hexabromodiphenyl ethane, from about 12 to about 25 area percent for heptabromodiphenyl ethane, 15–25 gas chromatographic area percent octabromodiphenyl ethane from about 10 to about 15 area percent for nonabromodiphenyl ethane and from about zero to about 5 area percent for decabromodiphenyl ethane.

5. An acrylonitrile-butadiene-styrene copolymer based formulation containing, in a flame retardant amount, the mixture of claim 1 and a predominate amount of an acrylonitrile-butadiene-styrene copolymer resin.

6. The acrylonitrile-butadiene-styrene copolymer based formulation of claim 5 wherein the formulation additionally contains a flame retardant synergist.

7. The acrylonitrile-butadiene-styrene copolymer based formulation of claim 5 wherein the mixture is present in an amount of from about 10 to about 30 weight percent and the acrylonitrile-butadiene-styrene copolymer resin is present in an amount of from about 70 to about 90 weight percent, all based upon the total weight of the formulation.

8. The acrylonitrile-butadiene-styrene copolymer based formulation of claim 7 wherein the formulation additionally contains from about 2 to about 6 weight percent of a flame retardant synergist.

9. The acrylonitrile-butadiene-styrene copolymer based formulation of claim 8 wherein the flame retardant synergist is Sb$_2$O$_3$.

10. An acrylonitrile-butadiene-styrene copolymer based formulation containing, in a flame retardant amount, the mixture of claim 3 and a predominate amount of an acrylonitrile-butadiene-styrene copolymer resin.

11. An acrylonitrile-butadiene-styrene copolymer based formulation containing, in a flame retardant amount, the mixture of claim 4 and a predominate amount of an acrylonitrile-butadiene-styrene copolymer resin.

12. The acrylonitrile-butadiene-styrene copolymer based formulation of claim 10 wherein the mixture is present in an amount of from about 10 to about 30 weight percent and the acrylonitrile-butadiene-styrene copolymer resin is present in an amount of from about 70 to about 90 weight percent, all based upon the total weight of the formulation.

13. The acrylonitrile-butadiene-styrene copolymer based formulation of claim 11 wherein the mixture is present in an amount of from about 10 to about 30 weight percent and the acrylonitrile-butadiene-styrene copolymer resin is present in an amount of from about 70 to about 90 weight percent, all based upon the total weight of the formulation.

14. The acrylonitrile-butadiene-styrene copolymer based formulation of claim 12 wherein the formulation additionally contains from about 2 to about 6 weight percent of a flame retardant synergist.

15. The acrylonitrile-butadiene-styrene copolymer based formulation of claim 13 wherein the formulation additionally contains from about 2 to about 6 weight percent of a flame retardant synergist.

16. An article formed from the acrylonitrile-butadiene-styrene copolymer based formulation of claim 10.

17. An article formed from the acrylonitrile-butadiene-styrene copolymer based formulation of claim 10.

18. An article formed from the acrylonitrile-butadiene-styrene copolymer based formulation of claim 11.

19. An article formed from the acrylonitrile-butadiene-styrene copolymer based formulation of claim 12.

20. An article formed from the acrylonitrile-butadiene-styrene copolymer based formulation of claim 13.

21. An article formed from the acrylonitrile-butadiene-styrene copolymer based formulation of claim 14.

22. An article formed from the acrylonitrile-butadiene-styrene copolymer based formulation of claim 15.

* * * * *

UNITED STATES PATENT AND TRADEMARK OFFICE
CERTIFICATE OF CORRECTION

PATENT NO. : 5,039,729

DATED : August 13, 1991

INVENTOR(S) : David R. Brackenridge et al.

It is certified that error appears in the above-identified patent and that said Letters Patent is hereby corrected as shown below:

```
Column 10, line 4, reads "formulation of Claim 10" and should
read -- formulation of Claim 5 --.
```

Signed and Sealed this

Twenty-third Day of February, 1993

Attest:

STEPHEN G. KUNIN

*Attesting Officer*   *Acting Commissioner of Patents and Trademarks*